US00PP32096P3

(12) United States Plant Patent
Danziger

(10) Patent No.: US PP32,096 P3
(45) Date of Patent: Aug. 18, 2020

(54) ***PETUNIA* PLANT NAMED 'DPETAMKOH'**

(50) Latin Name: ***Petunia sensu* Wijsman**
Varietal Denomination: DPETAMKOH

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,464

(22) Filed: Oct. 10, 2019

(65) Prior Publication Data

US 2020/0068769 P1 Feb. 27, 2020

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13
CPC ..... A01H 5/02; A01H 6/82
See application file for complete search history.

*Primary Examiner* — Annette H Para
(74) *Attorney, Agent, or Firm* — Cassandra Bright

(57) ABSTRACT

A new distinct cultivar of *Petunia* plant named 'DPETAMKOH' is disclosed, characterized by a mounded growth habit, and red flowers with white stripes. The plants are very well branched with a medium vigor. The new variety is a *Petunia*, normally produced as an outdoor garden or container plant.

2 Drawing Sheets

Figure 1:
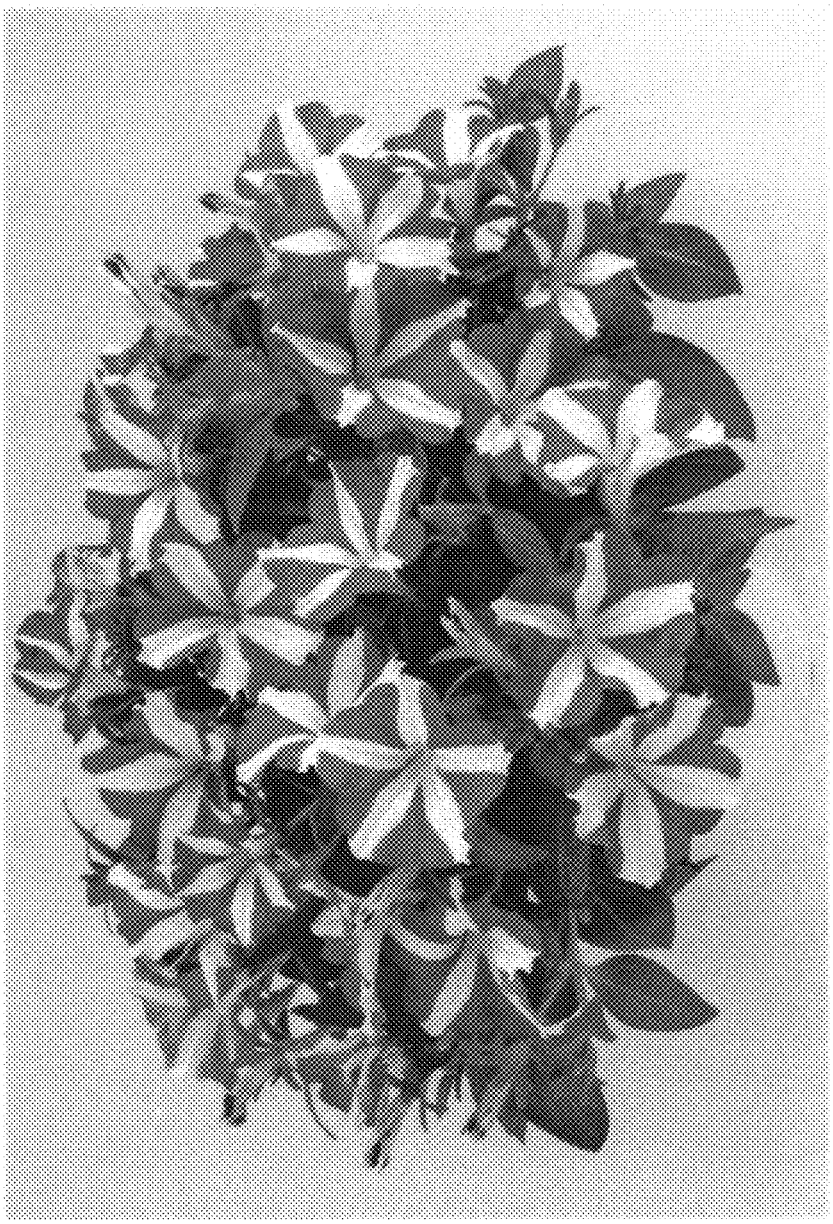

Latin name of the genus and species: *Petunia sensu* Wijsman.

Variety denomination: 'DPETAMKOH'.

BACKGROUND OF THE INVENTION

The new *Petunia* hybrid cultivar is a product of a planned breeding program conducted by the inventor, Gavriel Danziger in Moshav Mishmar Hashiva, Israel. The objective of the breeding program was to produce new *Petunia* varieties with interesting flower color patterns. The cross resulting in this new variety was made during September of 2016.

The seed parent is the unpatented, propriety variety referred to as *Petunia* 'cv.15-1200'. The pollen parent is the unpatented, propriety variety referred to as *Petunia* 'cv. 15-1174'. The new variety was discovered in June 2017 by the inventor in a group of seedlings resulting from the 2016 crossing, in a greenhouse in Moshav Mishmar Hashiva, Israel. Date of first sale was Nov. 4, 2018, occurring in the United States. This sale was made directly by the inventor or one who obtained the claimed invention directly or indirectly from the inventor. This sale and all public disclosures made between Nov. 4, 2018 and the filing of this application fall within the exception allowed under 102(b)(1).

Asexual reproduction of the new cultivar 'DPETAMKOH' was first performed by terminal vegetative cuttings during June 2017, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DPETAMKOH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPETAMKOH' These characteristics in combination distinguish 'DPETAMKOH' as a new and distinct *Petunia* cultivar:

1. Mounded growth habit.
2. Very well branched plant with medium vigor.
3. Flower color is red with white stripes.
4. Large flowers.
5. Abundant flowering.

PARENT COMPARISON

Plants of the new cultivar 'DPETAMKOH' are similar to plants of the seed parent in most horticultural characteristics, however, plants of the new cultivar 'DPETAMKOH' differ in the following;

1. The new variety has a mounded growth habit, while the seed parent is semi-upright.
2. New variety has medium vigor, while the seed parent is more vigorous.
3. New variety has red flowers with white stripes, while the seed parent has dark red flowers with white stripes.
4. New variety has smaller flowers than the seed parent.
5. New variety flowers more abundantly than the seed parent.

Plants of the new cultivar 'DPETAMKOH' are similar to plants of the pollen parent in most horticultural characteristics however, plants of the new cultivar 'DPETAMKOH' differ in the following;

1. The new variety has a mounded growth habit, while the pollen parent is semi-trailing.
2. Pollen parent is more compact than the new variety.
3. New variety has red flowers with white stripes, while the pollen parent has pink flowers with white stripes.

4. New variety has larger flowers than the pollen parent.
5. New variety flowers more abundantly than the pollen parent.

COMMERCIAL COMPARISON

Plants of the new cultivar 'DPETAMKOH' can be compared to the commercial variety *Petunia 'DAMORQUEEN', U.S. Plant Pat. No.* 29,020. These varieties are similar in most horticultural characteristics; however, 'DPETAMKOH' differs in the following:

1. Flower color of the comparison variety is red with yellow stripes, while the new variety has red flowers with white stripes
2. Flower throat color of the comparison variety is red with yellow stripes, while the new variety has a light yellow-green throat.
3. New variety has larger flowers than this comparator.

Plants of the new cultivar 'DPETAMKOH' can also be compared to the commercial variety *Petunia* 'DAMORJOY', U.S. Plant Pat. No. 29,310. These varieties are similar in most horticultural characteristics; however, 'DPETAMKOH' differs in the following:

1. Flower color of the comparison variety is purple with white stripes, while the new variety has red flowers with white stripes.
2. Flower throat color of the comparison variety is light green with purple stripes, while the new variety has a light yellow-green throat.

BRIEF DESCRIPTION OF THE PHOTOGRAPHS

The accompanying photograph in FIG. 1 illustrates in full color a typical plant of 'DPETAMKOH' grown in a greenhouse, in Moshav Mishmar Hashiva, Israel.

Figure 2:
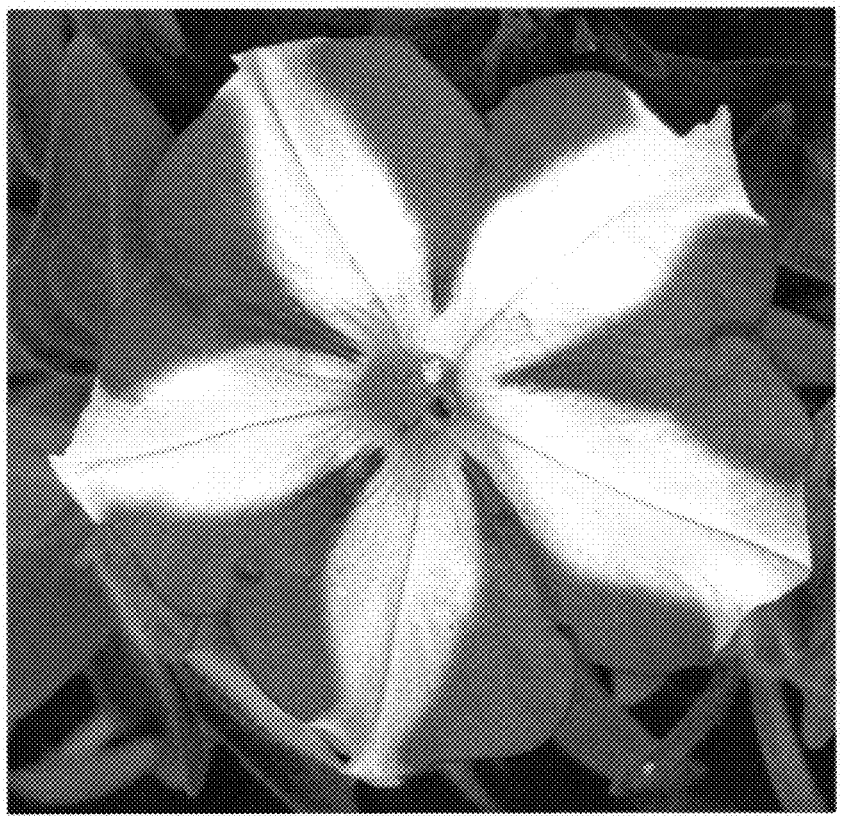

FIG. 2 illustrates in full color a typical mature flower of 'DPETAMKOH' during Spring. Age of the plant photographed is approximately 6 months from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPETAMKOH' plants grown in greenhouse in Moshav Mishmar Hashiva, Israel, under natural lighting. Measurements were taken during April of 2019. The plants were approximately 60 days from a rooted cutting in a 20 cm pot. The growing temperature ranged from 20° C. to 35° C. during the days, 17° C. to 23° C. during the nights. Measurements and numerical values represent averages of typical plant types.

Botanical classification: *Petunia sensu* Wijsman 'DPETAMKOH'.

PROPAGATION

Time to initiate roots: 10 to 14 days at approximately 20° C.
Root description: Fibrous.

PLANT

Growth habit: Mounded.
Pot size of plant described: 13 cm.
Height: About 25 cm to top of flowering plane.
Plant spread: About 55 cm.
Growth rate.: Medium.
Branching characteristics: Very well branched.
Length of primary lateral branches: About 27 cm.
Diameter of lateral branches: About 0.3 cm.
Quantity of primary lateral branches: 8.
Characteristics of primary lateral branches:
- *Form*.—Cylindrical.
- *Diameter*.—About 0.3 cm.
- *Color*.—RHS Yellow-Green 144B.
- *Texture*.—Pubescent.
- *Strength*.—Strong.

Internode length: About 1.5 cm.

FOLIAGE

Leaf:
- *Arrangement*.—Opposite.
- *Quantity*.—Approximately 30 per branch.
- *Average length*.—5.5 cm.
- *Average width*.—2.5 cm.
- *Shape of blade*.—Elliptic.
- *Apex*.—Acute.
- *Base*.—Acute.
- *Margin*.—Entire.
- *Texture of top surface*.—Velvety pubescence.
- *Texture of bottom surface*.—Velvety pubescence.
- *Aspect*.—90° attachment, mostly flat or slight downward curve.
- *Color*.—Young foliage upper side: RHS Yellow-Green 146A. Young foliage under side: RHS Yellow-Green 146B. Mature foliage upper side: RHS Yellow-Green 146A. Mature foliage under side: RHS Yellow-Green 146B.
- *Venation*.—Type: Pinnate. Venation color upper side: RHS Yellow-Green 146B. Venation color under side: RHS Yellow-Green 146C.
- *Petiole*.—Length: About 0.7 cm. Diameter: About 0.3 cm. Color: RHS Yellow-Green 146B. Texture: Velvety.

FLOWER

Natural flowering season: Spring, Summer, and Autumn in Mishmar Hashiva, Israel.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3 to 6 days.
Approximate quantity of flowers per plant: About 70.
Persistent or self-cleaning: Self-cleaning.
Bud:
- *Shape*.—Tubular.
- *Length*.—About 4.5 cm.
- *Diameter*.—About 0.8 cm.
- *Color*.—RHS Yellow-Green 154C, tip Red-Purple 60B.

Flower size:
- *Diameter*.—About 6.5 cm.
- *Length*.—About 2.5 cm.
- *Flower tube diameter at distal end*.—About 1.1 cm.
- *Flower tube diameter at proximal end*.—About 0.3 cm.

Petals:
*Length from throat.*—About 2.7 cm.
*Width.*—About 2.8 cm.
*Quantity.*—5.
*Texture.*—Velvety all surfaces.
*Apex.*—Acute.
*Margin.*—Entire.
Color:
*When opening.*—Upper surface: RHS Red 45A, with 5 stripes, White NN155C. Lower surface: RHS Red 45C, with 5 stripes, White NN155C.
*Fully opened.*—Upper surface: Between RHS Red 45B, with 5 stripes, White NN155C. Lower surface: RHS Red 45D, with 5 stripes, White NN155C. Flower throat (inside): RHS Yellow-Green N144D. Flower throat, vein: RHS Yellow-Green N144C and Red-Purple 59B. Flower tube (outside): RHS Yellow-Green 145C. Flower tube, vein: RHS Yellow-Green 145A.
*Fading.*—RHS Red 45D with 5 stripes, White NN155C.
Calyx/sepals:
*Quantity per flower.*—5.
*Shape.*—Linear.
*Length.*—About 2.2 cm.
*Width.*—About 0.3 cm.
*Apex.*—Acute.
*Base.*—Cuneate.
*Margin.*—Entire.
*Texture.*—Velvety.
*Color.*—Upper Surface: RHS Yellow-Green 146A. Lower Surface: RHS Yellow-Green 146B.
Peduncle: Not present.
Pedicel:
*Length.*—About 2.5 cm.
*Diameter.*—About 0.2 cm.
*Color.*—RHS Yellow-Green 146D.
*Orientation.*—45°.
Fragrance: None.

REPRODUCTIVE ORGANS

Stamens:
*Number.*—5.
*Filament length.*—About 2 cm.
Anthers:
*Length.*—About 0.1 cm.
*Shape.*—Rounded.
*Color.*—RHS Yellow 10D.
*Pollen.*—Color: RHS Yellow 10C. Quantity: Plenty.
Pistil:
*Number.*—1.
*Length.*—About 2.6 cm.
*Style.*—Length: About 2 cm. Color: RHS Yellow-Green 150C.
*Stigma.*—Shape: Rounded. Color: RHS Yellow-Green 144B. Ovary Color: RHS Yellow-Green 144C.

OTHER CHARACTERISTICS

Seeds and fruits: About 80 dark brown, rounded seeds of about 0.5 mm diameter, per one conical capsule. Colored near Brown 200B.
Disease/pest resistance: Neither resistance nor susceptibility to normal diseases and pests of *Petunia* observed to date.
Temperature tolerance: Tolerates a range between 5° C. to 40° C.

What is claimed is:
1. A new and distinct cultivar of *Petunia* plant named 'DPETAMKOH' as herein illustrated and described.

* * * * *